(12) United States Patent
Vipulanandan

(10) Patent No.: US 10,481,143 B2
(45) Date of Patent: Nov. 19, 2019

(54) CHEMO-THERMO-PIEZORESISTIVE HIGHLY SENSING SMART CEMENT WITH INTEGRATED REAL-TIME MONITORING SYSTEM

(71) Applicant: University of Houston System, Houston, TX (US)

(72) Inventor: Cumaraswamy Vipulanandan, The Woodlands, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 15/745,558

(22) PCT Filed: Jul. 12, 2016

(86) PCT No.: PCT/US2016/041905
§ 371 (c)(1),
(2) Date: Jan. 17, 2018

(87) PCT Pub. No.: WO2017/011460
PCT Pub. Date: Jan. 19, 2017

(65) Prior Publication Data
US 2018/0209951 A1 Jul. 26, 2018

Related U.S. Application Data

(60) Provisional application No. 62/192,010, filed on Jul. 13, 2015.

(51) Int. Cl.
*E21B 33/14* (2006.01)
*G01N 33/38* (2006.01)

(52) U.S. Cl.
CPC ............ *G01N 33/383* (2013.01); *E21B 33/14* (2013.01)

(58) Field of Classification Search
CPC .............................. E21B 33/14; G01N 33/383
(Continued)

(56) References Cited

U.S. PATENT DOCUMENTS

2010/0045311 A1  2/2010  Chung
2012/0094028 A1*  4/2012  Briand .................... B05D 1/34
                                                        427/427.4

(Continued)

FOREIGN PATENT DOCUMENTS

WO       2015/077524       5/2015

OTHER PUBLICATIONS

Notification Concerning Transmittal of International Preliminary Report on Patentability and Written Opinion of the Korean Intellectual Property Office for International Application No. PCT/US2016/041905, mailed by the International Bureau of WIPO, dated Jan. 25, 2018, 8 pages.

(Continued)

*Primary Examiner* — Silvana C Runyan
(74) *Attorney, Agent, or Firm* — Jackson Walker LLP

(57) ABSTRACT

The chemo-thermo-piezoresistive behavior of so-called "smart cement," or cement modified with conductive fillers, is useful as a bulk sensor for monitoring the changes in the cement due to stresses, cracks, contamination, fluid loss, and temperature change that affect its performance. The smart cement utilizes a special conductive or semi-conductive filler and is useful as a bulk sensor that allows real-time monitoring of its properties.

12 Claims, 9 Drawing Sheets

(58) Field of Classification Search
USPC .......................................................... 166/292
See application file for complete search history.

(56) References Cited

U.S. PATENT DOCUMENTS

2014/0318783 A1    10/2014  Martin et al.
2016/0265183 A1*    9/2016  Karsten ................ E02D 17/207

OTHER PUBLICATIONS

Transmittal of the Extended European Search Report as mailed by the European Patent Office dated Feb. 26, 2019 for European Patent Application No. 16825014.1, 8 pages.
Vipulanandan, "Development of Smart Cement for Real Time Monitoring of Ultra Deepwater Oil Well Cementing Applications", Proceedings CIGMAT-2014 Conference & Exhibition, Jan. 1, 2014, 16 pages.

* cited by examiner

CHEMO-THERMO-PIEZORESISTIVE HIGHLY SENSING SMART CEMENT WITH INTEGRATED REAL-TIME MONITORING SYSTEM

This application claims priority to U.S. Provisional Patent Application Ser. No. 62/192,010, filed on Jul. 13, 2015, entitled "Piezo-Chemi-Resistive Highly Sensing Smart Cement with Integrated Real-Time Monitoring System," the entire contents of which are hereby incorporated by reference.

The present invention used in part funds from the Department of Energy (DOE), Research Partnership to Secure Energy for America (RPSEA), Project No. 10121-4501-01. The United States Government has certain rights in the invention.

BACKGROUND

The present invention relates to the development and application of chemo-thermo-piezoresistive smart cement with bulk sensing properties to measure the changes in the electrical properties of the smart cement in order to monitor its integrity and performance in real-time.

Oil well cement serves many purposes in the deep water drilling projects. Foremost important among these is to form a sealing layer between the well casing and the geological formation referred to as the zonal isolation. For successful oil well and gas well cementing operations, it is critical to determine the flowing of cement slurry between the casing and formation, depth of the circulation losses and fluid loss, setting of cement in place and performance of the cement after hardening. In the civil infrastructures (foundations, piles, pipelines, bridges, highways, storage facilities and buildings) Portland cement serves many purposes for successful construction and/or repairing applications. Hence it is critical to determine the hardening of the cement and monitoring the conditions in the cement throughout the entire service life.

Two studies done on blowouts on the U.S. outer continental shelf (OCS) during the period of 1971 to 1991 and 1992 to 2006 clearly identified cementing failures as the major cause for blowouts (Izon et al. 2007). Cementing failures increased significantly during the second period of study when 18 of the 39 blowouts were due to cementing problems (Izon et al. 2007). Also the deep-water horizon blowout in 2010 in the Gulf of Mexico was due to cementing issues (Kyle et al. 2014). With some of the reported failures and growing interest in environmental and economic concerns in the oil and gas industry and civil infrastructures, integrity of the cemented materials are of major importance. Therefore, proper monitoring and tracking the entire process of well cementing and other cementing operations become important to ensure cement integrity during the service life (Vipulanandan et al. 2014a-d). At present there is no technology available to monitor cementing/coating/concreting operations in real time from the time of placement through the service life of the applications. Also during the oil and gas well installation, there is no reliable method to determine the length of the competent of cement supporting the casing.

The API and ASTM tests for cementing include procedures for finding density, free water, fluid loss, rheological properties and compressive strength. All these tests are important for composing a successful cement grout, but most of them consider only one (thickening time) or a few points of time during the setting process. Several non-destructive methods (X-ray diffraction, calorimetric analysis, scanning electron microscopy and ultrasonic methods) have been used by researchers to monitor the curing and characterize the behavior of cementitious materials (Vipulanandan et al. 2014a,b). Electrical resistivity measurement has been used by many researchers for characterizing concrete and cementitious grouts for various applications (McCarter 1996; Wei et al. 2008; Azhari et al. 2012; Han et al. 2012; Vipulanandan et al. 2014a-c; Liao et al. 2014). The advantages in using the electrical resistivity to characterize the material include its sensitivity to changes and relatively easy measure. Electrical resistivity of cement is affected by a number of factors such as pore structure, pore solution composition, cementitious content, w/c ratio, moisture content and temperature (McCarter 1994; Vipulanandan et al. 2014a,b). Electrical conduction occurs primarily due to ion transport through the pore solution in a cement-based system and hence strongly depends on both pore solution conductivity and porosity (Wei et al. 2008). Therefore chemical reactions and change in microstructure of cement during the hydration process affects the electrical resistivity response of the cement-based composites (Zuo et al. 2014; Vipulanandan et al. 2014b).

Past studies have reported that the interfacial factors are important in obtaining electrical resistivity from electrical resistance (Chung 2001). Due to the voltage present during electrical resistance measurement, electric polarization occurs as the resistance measurement is made continuously. The polarization results in an increase in the measured resistance. The conventional methods of measuring the electrical resistivity of cementitious materials can be categorized into direct-current (DC) methods and alternating-current (AC) methods, both of which require electrodes for their measurements. Therefore, there is the potential for contact problems between the electrodes and the matrix, which could completely affect the accuracy of the measurement. Recent studies have suggested that replacing the DC measurement with the AC measurement can eliminate the polarization effect (Zhang et al. 2010, Vipulanandan et al. 2013). It has been observed that the relationship between resistivity and curing time for various types of cement grouts followed a similar pattern (Wei et al. 2008; Vipulanandan et al. 2014a-c). The electrical resistivity dropped to a minimum value, and then gradually increased with time. Initially after mixing cement with water, resistivity decreased to a minimum value ($\rho_{min}$), and the corresponding time to reach the minimum resistivity was ($t_{min}$). The $t_{min}$ can be used as an index for the speed of chemical reactions and cement setting times. Also the electrical resistivity is predominated by the conductivity of the pore solution and the connectivity of pores Immediately after mixing, the pores are connected and more conduction paths are formed between cement particles. After 24 hours of curing the hydration products block the conduction path and tortuosity increases. The decrease of connectivity of pores results in a sharp increase in the resistivity curve (Wei et al. 2008; Vipulanandan et al. 2014a-c). However, there is very limited information in the literature about quantification of the electrical resistivity during curing of the oil well cements. As the porosity decreases due to shrinkage and increased accumulation of hydration products in the cement grout pores there is increase in compressive strength.

SUMMARY

The present disclosure relates generally to so-called "smart cement," or cement modified with conductive fillers (no nanoparticles) to enhance the chemo-thermo-piezoresistive behavior of such smart cement in determining and monitoring properties such as changes in stresses, hydration, contamination, formation of cracks and fluid losses.

Smart cement is a highly sensing material. The sensing property is electrical resistivity. The sensing properties changes with stress, contamination, cracks, fluid loss and temperature. Based on the application the degree of sensing required could be different. Also the type of conductive filler could be different based on the application. For cement to be chemo-thermo-piezoresistive the conductive fiber content should be between about 0.03% to about 0.1% based on the weight of cement.

In civil infrastructures, there are no bulk sensors (these are not embedded foreign sensors) and hence the smart cement can be used as a bulk sensor to monitor the hardening of concrete, coatings or grouts and the performance during the entire service life.

Past studies have investigated the changes in electrical resistivity with applied stress referred to as piezoresistive behavior of modified cement-based and polymer composites (Vipulanandan et al. 2008). The studies showed that the changes in resistivity with the applied stress were 30 to 50 times higher than the strain in the materials. Hence the change in resistivity has the potential to be used to determine the integrity of the materials and modeling the non linear behavior of the smart cement is important to better understand the effects of various parameters investigated in the study (Zuo et al. 2014; Vipulanandan et al. 2002-2014a-c).

In conjunction with the present disclosure, the sensing properties for the cement that can be used to monitor the performance of the smart cement were identified. After numerous studies and based on the current study on oil well cements and Portland cement, electrical resistivity ($\rho$) was selected as the sensing property for cement-based materials. Hence two parameters (resistivity and change in resistivity) were used to quantify the sensing properties of cement. Electrical resistivity is given by:

$$R = \rho(L/A) = \rho K$$

where R is electrical resistance, L is the linear distance between the electrical resistance measuring points, A is the effective cross sectional area and K is calibration parameter determined based on the resistance measurement method measured at 300 kHz of frequency. Normalized change in resistivity with the changing conditions is represented as:

$$\frac{\Delta \rho}{\rho_0} = \frac{\Delta R}{R_0},$$

where $R_o$, $\rho_o$: Initial resistance and resistivity and $\Delta R$, $\Delta \rho$: change in resistance and change in resistivity.

Monitoring the integrity and performance of smart cement will include measuring the total resistivity ($\rho_0$) and the rate of resistivity change ($\Delta \rho$). By determining $R_b$ at 300 kHz or higher frequency, the resistance can be determined (Vipulanandan et al. 2013 and 2014a,b). The total resistivity is determined by using the calibration parameter K with the measured resistance, as shown above.

Understanding the sensing properties of the smart cement permits the use of such cement in conjunction with a method and system for monitoring and tracking its physical properties. This disclosure utilizes a bulk sensor concept (chemo-thermo-piezoresistive) and identified monitoring parameters. A special conductive filler, which makes up less than about 0.1% of the cement, is used. The special conductive filler is a modified product made up of dispersed carbon fibers or basaltic fibers. The monitoring system is utilized in real-time and may involve the placement of flexible wires extending from portions of the cement. The changes can be quantified based on the chemo-thermo-piezoresistive properties and can produce very highly sensing cement. In addition, contamination of the cement can be detected using the present method.

Based on the change in resistivity, the stress in the smart cement can be determined using the p-q piezoresistive constitutive model as follows:

$$\frac{\sigma}{\sigma_f} = \left[ \frac{\frac{x}{x_f}}{q_2 + (1 - p_2 - q_2)\frac{x}{x_f} + p_2 \left(\frac{x}{x_f}\right)^{\left(\frac{p_2}{p_2 - q_2}\right)}} \right],$$

where $\sigma$: stress (psi); $\sigma_f$: stress at failure (psi);

$$x = \left(\frac{\Delta \rho}{\rho_0}\right) * 100 =$$

Percentage of change in electrical resistivity due to the stress;

$$x_f = \left(\frac{\Delta \rho}{\rho_0}\right)_f * 100 = \text{Percentage of change}$$

in electrical resistivity at failure;

$\Delta \rho$: change in electrical resistivity;

$\rho_0$: Initial electrical resistivity ($\sigma = 0$ MPa) and $p_2$ and $q_2$ are piezoresistive model parameters.

When the slurry resistivity changes rapidly by 20% or more during the initial installation, the cement could be contaminated. The rapid change in resistivity depends on the type and amount of contamination.

Behavior of the smart cement can be monitored at various stages of construction and during the service life of the structure, particularly oil wells, foundations, piles, pipelines, bridges, highways, storage facilities and buildings. The chemo-thermo-piezoresistive smart cement may also be used as part of any grout, concrete, coating, or repair material. The piezoresistive behavior of the present smart cement has been substantially improved without affecting the cement's rheological and setting properties. For the smart cement, the resistivity change at peak compressive stress is over 1000 times higher than the change in the strain (which was only 0.2%).

DETAILED DESCRIPTION OF PREFERRED EMBODIMENTS

Figure 1:
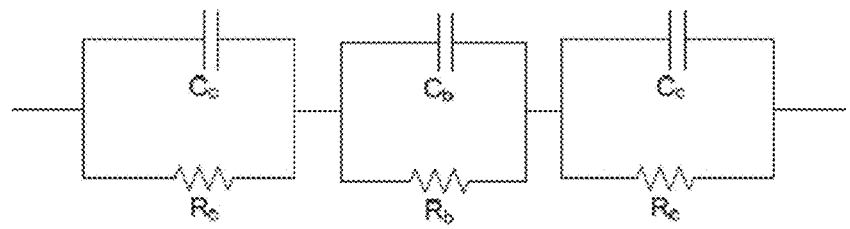
FIG. 1 shows an example equivalent circuit representing electrical properties of smart cement.

The present disclosure relates to a smart cement modified with conductive fillers and the use of chemo-thermo-piezoresistive behavior as an indicator of its structural properties and degradations.

In preferred embodiments, a system for monitoring performance-related properties of cement is described. The system includes a cement structure comprised of smart cement, wherein the smart cement comprises from about 0.03% to about 0.1% modified conductive filler by weight of the cement, and wherein the modified conductive filler comprises dispersed carbon fibers, dispersed basaltic fibers, or mixtures thereof. The system also includes an integrated monitoring system for monitoring electrical properties of the smart cement, wherein the electrical properties of the smart cement are correlated with performance-related properties of the cement.

The modified conductive and/or semi-conductive filler can include dispersed carbon fibers or dispersed basaltic fibers, or mixtures of the two. The fibers typically have a length to diameter ratio of 10 or more. Nanoparticles are not used in the smart cement, making it environmentally acceptable. The fibers that make up the modified conductive filler can be obtained commercially as carbon fibers (e.g., Zoltek PANEX® carbon fibers, St. Louis, Mo.) or basalt fibers (e.g., Sudaglass Fiber Technology, Inc. basalt fibers, Houston, Tex.). The fibers are preferably mixed in surfactant solutions or hot water and blended in mixers for dispersion and then dried before using them in the cement.

Smart cement can be prepared in several ways. The main objective is to disperse the fibers in the cement very well. A first simple example is as follows: Disperse the fibers in water. Add cement and mix. The resistivity of the smart cement slurry will be about 1 Ω·m depending on the water-to-cement ratio. A second example is as follows: Mix the fibers with dry cement. Add water and mix the cement with fiber addition. The resistivity of the smart cement slurry will be about 1 Ω·m depending on the water-to-cement ratio.

EXAMPLE 1

Electrical Resistivity Measurements

Two different methods were investigated for electrical resistivity measurements of oil well cement slurries. To assure the repeatability of the measurements, the initial resistivity was measured at least three times for each cement slurry and the average resistivity was reported. The electrical resistivity of the cement slurries were measured using: (i) Conductivity Probe and (ii) Digital Resistivity Meter. A commercially available conductivity probe was used to measure the conductivity (inverse of resistivity) of the slurries. In the case of cement, this meter was used during the initial curing of the cement. The conductivity measuring range was from 0.1 µS/cm to 1000 mS/cm, representing a resistivity of 0.1 Ω·m to 10,000 Ω·m. A digital resistivity meter (used in the oil industry) was used measure the resistivity of fluids, slurries and semi-solids directly. The resistivity range for this device was 0.01 Ω–m to 400 Ω–m. The conductivity probe and the digital electrical resistivity device were calibrated using a standard solution of sodium chloride (NaCl).

EXAMPLE 2

Impedance Spectroscopy Model

Identification of the most appropriate equivalent circuit to represent the electrical properties of a material and interface corrosion is essential to further understand its properties. In this study, an equivalent circuit to represent the smart cement was required for better characterization through the analyses of the impedance spectroscopy data. It was necessary to make a link between the different elements in the circuit and the different regions in the impedance data of the corresponding sample. Given the difficulties and uncertainties, researchers tend to use a pragmatic approach and adopt a circuit which they believe to be most appropriate from their knowledge of the expected behavior of the material under study, and demonstrate that the results are consistent with the circuit used. In this example, different possible equivalent circuits were analyzed to find an appropriate equivalent circuit to represent the smart cement and, as applicable, smart drilling mud.

In a first case (Case 1), the contacts were connected in series, and both the contacts and the bulk material were represented using a capacitor and a resistor connected in parallel.

In the equivalent circuit for Case 1, shown in FIG. 1, $R_b$ and $C_b$ are resistance and capacitance of the bulk material, respectively, and $R_c$ and $C_c$ are resistance and capacitance of the contacts, respectively. Both contacts are represented with the same resistance ($R_c$) and capacitance ($C_c$) as they are identical. Total impedance of the equivalent circuit for Case 1 ($Z_1$) can be represented as follows:

$$Z_1 = \frac{R_b}{1+\omega^2 R_b^2 C_b^2} + \frac{2R_c}{1+\omega^2 R_c^2 C_c^2} - j\left\{\frac{2\omega R_c^2 C_c}{1+\omega^2 R_c^2 C_c^2} + \frac{\omega R_b^2 C_b}{1+\omega^2 R_b^2 C_b^2}\right\},$$

where ω is the angular frequency of the applied signal. When the frequency of the applied signal was very low, ω→0, $Z_1=R_b+2R_c$, and when it is very high, ω→∞, $Z_1=0$.

Figure 2:
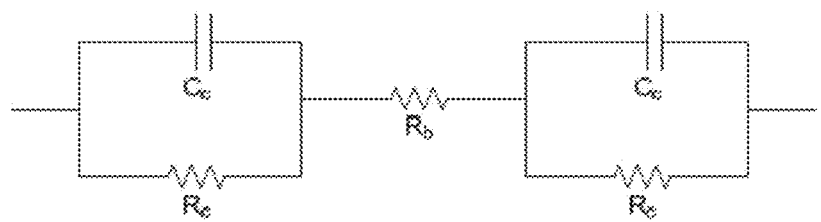
FIG. 2 shows an example equivalent circuit representing electrical properties of smart cement.

In a second case (Case 2), which is a special case of Case 1, the capacitance of the bulk material ($C_b$) was assumed to be negligible. The equivalent circuit is shown in FIG. 2. The total impedance of the equivalent circuit for Case 2 ($Z_2$) is as follows:

$$Z_2(\sigma) = R_b(\sigma) + \frac{2R_c(\sigma)}{1+\omega^2 R_c^2 C_c^2} - j\frac{2\omega R_c^2 C_c(\sigma)}{1+\omega^2 R_c^2 C_c^2}$$

Figure 3:
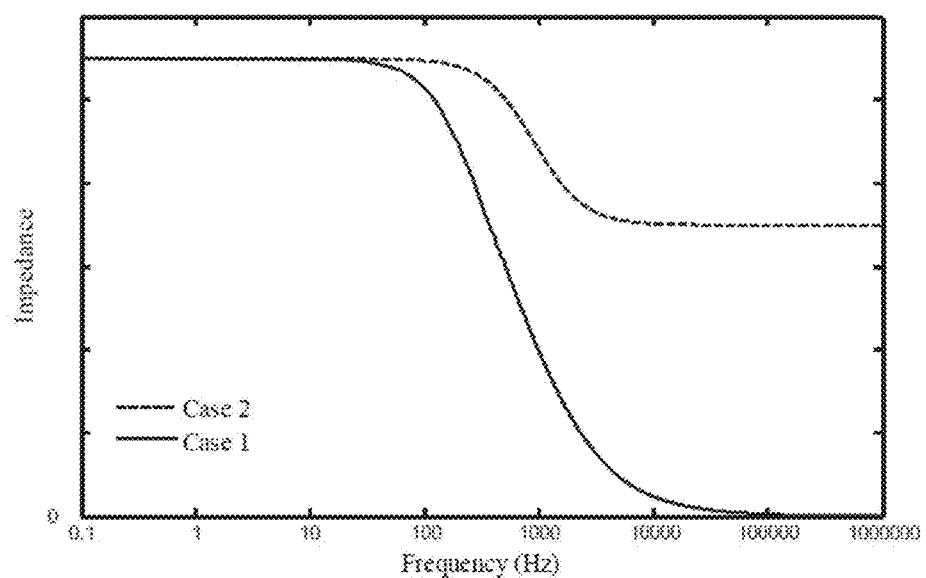
FIG. 3 shows a comparison of typical impedance versus frequency responses of example equivalent circuit.

When the frequency of the applied signal was very low, ω→0, $Z_2=R_b+2R_c$, and when it is very high, ω→∞, $Z_2=R_b$ (FIG. 3).

FIG. 3 shows a comparison of typical responses for the equivalent circuits for Case 1 and Case 2. Testing indicated that Case 2 represented the behavior in the frequency range of 20 Hz to 300 kHz at a frequency of 300 kHz.

EXAMPLE 3

Testing and Characterization

In this study, oil well cement and Portland cement with water-to-cement of 0.38, 0.44 and 0.54 was used. The samples were prepared according to the API and ASTM standards. To improve the sensing properties and piezoresistive behavior of the cement modified with 0.1% of conductive fillers (CF) by the weight of cement was mixed with all the samples. After mixing, specimens were prepared using cylindrical molds with diameter of 50 mm and a height of 100 mm Two conductive wires were placed in all of the molds to measure the changing in electrical resistivity. At least three specimens were prepared for each mix.

For the compressive strength test, the cylindrical specimen (50 mm dia.*100 mm height) was capped and tested at a predetermined controlled displacement rate. Compression tests were performed on cement samples after 1, 7 and 28 days of curing using a hydraulic compression machine. At least three specimens were tested under each testing condition and average results were reported.

Piezoresistivity describes the change in electrical resistivity of a material under stress. Since oil well cement serves as pressure-bearing part of the oil and gas wells in real applications, the piezoresistivity of smart cement (stress-resistivity relationship) with different w/c ratios were investigated under compressive loading at different curing times. During the compression test, electrical resistance was measured in the direction of the applied stress. To eliminate the polarization effect, AC resistance measurements were made using a LCR meter at frequency of 300 kHz (Vipulanandan et al. 2013).

In order to determine the accuracy of the model predictions, both coefficient of determination ($R^2$) and the root mean square error (RMSE) in curve fitting as defined in the equations below were quantified.

$$RMSE = \sqrt{\frac{\sum_{i=1}^{n}(y_i - x_i)^2}{N}}$$

$$R^2 = \left(\frac{\Sigma_i(x_i - \bar{x})(y_i - \bar{y})}{\sqrt{\Sigma_i(x_i - \bar{x})^2} * \sqrt{\Sigma_i(y_i - \bar{y})^2}}\right)^2,$$

where $y_i$=actual value; $x_i$=calculated value from the model; $\bar{y}$=mean of actual values; $\bar{x}$=mean of calculated values and N is the number of data points.

Several characteristic resistivity parameters can be used in monitoring the curing (hardening process) of the cement. The parameters are initial resistivity ($\rho o$), minimum electrical resistivity ($\rho min$), time to reach the minimum resistivity (tmin) and percentage of maximum change in resistivities at the end of 24 hours ($RI_{24\ hr}$) and 7 days ($RI_{7\ days}$) were defined in the equations below as follows:

$$RI_{24hr} = \frac{\rho_{24hr} - \rho_{min}}{\rho_{min}} * 100$$

$$RI_{7days} = \frac{\rho_{7days} - \rho_{min}}{\rho_{min}} * 100$$

(a) w/c=0.38

Unit weight of the smart cement with w/c of 0.38 was 16.48 ppg. The initial electrical resistivity ($\rho_o$) of the smart cement with w/c ratio of 0.38 modified with 0.1% CF was 1.03 Ω–m and the electrical resistivity reduced to reach the $\rho_{min}$ of 0.99 Ω–m after 99 minutes ($t_{min}$) as summarized in Table 1 below. The 24 hours electrical resistivity ($\rho_{24\ hr}$) of the cement was 4.15 Ω·m. Hence the maximum change in electrical resistivity after 24 hours ($RI_{24\ hr}$) was 319% as summarized in Table 1. The 7 days electrical resistivity ($\rho_{7\ days}$) of the cement grout was 7.75 Ω·m, hence the maximum change in electrical resistivity after 7 days ($RI_{7\ days}$) was 683%.

(b) w/c=0.44

Unit weight of the smart cement with w/c of 0.44 was 16.12 ppg. The initial electrical resistivity ($\rho_o$) of the smart cement with w/c ratio of 0.44 and modified with 0.1% CF was 1 Ω–m. The electrical resistivity reduced to reach the $\rho_{min}$ of 0.89 Ω–m after 114 minutes ($t_{min}$) as summarized in Table 1 below. The 24 hours electrical resistivity ($\rho_{24\ hr}$) of the sample was 2.55 Ω·m. Hence the maximum change in electrical resistivity after 24 hours ($RI_{24\ hr}$) was 187%. The 7 days electrical resistivity ($\rho_{7\ days}$) of the sample was 5 Ω·m, hence the maximum change in electrical resistivity after 7 days ($RI_{7\ days}$) was 462%.

(c) w/c=0.54

Unit weight of the smart cement with w/c of 0.38 was 15.78 ppg. The initial electrical resistivity ($\rho_o$) of the smart cement with w/c ratio of 0.54 modified with 0.1% CF was 0.9 Ω–m and the electrical resistivity reduced to reach the ρmin of 0.78 Ω–m after 128 minutes ($t_{min}$) as summarized in Table 1 below. The 24 hours electrical resistivity ($\rho_{24\ hr}$) of the sample was 1.67 Ω·m. Hence the maximum change in electrical resistivity after 24 hours ($RI_{24\ hr}$) was 114% as summarized in Table 1. The 7 days electrical resistivity ($\rho_{7\ days}$) of the sample was 4.6 Ω·m, hence the maximum change in electrical resistivity after 7 days ($RI_{7\ days}$) was 490%.

TABLE 1

| w/c | Density (ppg) | Initial resistivity, $\rho_o$ (Ω · m) | $\rho_{min}$ (Ω · m) | $t_{min}$ (min) | $\rho_{24\ hr}$ (Ω · m) | $\rho_{7\ days}$ (Ω · m) | $RI_{24\ hr}$ (%) | $RI_{7\ days}$ (%) |
|---|---|---|---|---|---|---|---|---|
| 0.38 | 16.48 | 1.03 | 0.99 | 99 | 4.15 | 7.75 | 319 | 683 |
| 0.44 | 16.12 | 1.0 | 0.89 | 114 | 2.55 | 5.0 | 187 | 462 |
| 0.54 | 15.78 | 0.9 | 0.78 | 128 | 1.67 | 4.6 | 114 | 490 |

The initial electrical resistivity ($\rho_o$) of the smart cement decreased by 3% and 13% when the w/c ratio increased from 0.38 to 0.44 and 0.54 respectively as summarized in Table 1. The minimum electrical resistivity ($\rho_{min}$) of the smart cement also decreased by 10% and 21% when the w/c ratio was increased from 0.38 to 0.44 and 0.54 respectively as summarized in Table 1. The time to reach the minimum electrical resistivity ($t_{min}$) increased by 15% and 21% when the w/c ratio increased from 0.38 to 0.44 and 0.54 respectively as summarized in Table 1.

The parameters $t_{min}$ and $\rho_{min}$ can be used as quality control indices and were related to the w/c ratio as follows:

$$t_{min} = 59.2\left(\frac{w}{c}\right) + 57 \quad R^2 = 0.87$$

$$\rho_{min} = 1.4 - 1.2\left(\frac{w}{c}\right) \quad R^2 = 0.94$$

Hence the electrical resistivity parameters were linearly related to the w/c ratio.

An additional 0.1% conductive filler substantially improved piezoresistive behavior of the cement. Based on experimental results, p-q model Vipulanandan and Paul (1990) was modified and used to predict the change in electrical resistivity of cement during with applied stress for 1, 7 and 28 days of curing. The new piezoresistive constitutive model (stress-resistivity relationship) was defined as follows:

$$\frac{\sigma}{\sigma_f} = \left[\frac{\frac{x}{x_f}}{q_2 + (1 - p_2 - q_2)\frac{x}{x_f} + p_2\left(\frac{x}{x_f}\right)^{\left(\frac{p_2}{p_2 - q_2}\right)}}\right],$$

where $\sigma$: stress (psi); $\sigma_f$: stress at failure (psi);

$$x = \left(\frac{\Delta\rho}{\rho_o}\right) * 100 =$$

Percentage of change in electrical resistivity due to the stress;

$$x_f = \left(\frac{\Delta\rho}{\rho_o}\right)_f * 100 = \text{Percentage of change}$$

in electrical resistivity at failure;

$\Delta\rho$: change in electrical resistivity;

$\rho_o$: Initial electrical resistivity($\sigma = 0$ MPa) and $p_2$ and $q_2$ are piezoresistive model parameters.

(i) 1 Day of Curing

The compressive strength ($\sigma_f$) of the cement with w/c ratio of 0.38, 0.44 and 0.54 for one day of curing were 10.6 MPa, 8.4 MPa and 4.6 MPa respectively, a 14% and 53% reduction when the w/c ratio increased from 0.38 to 0.44 and 0.54 respectively as summarized in Table 2 below. Addition of 0.1% CF to the cement (smart cement) with w/c ratio of 0.38, 0.44 and 0.54 increased the compressive strength to 10.9 MPa, 9.8 MPa and 5.3 MPa respectively. Hence the addition of 0.1% CF increased the strength by 3%, 17% and 15% for cement with w/c ratio of 0.38, 0.44 and 0.54 respectively as summarized in Table 2 below.

TABLE 2

| Material | w/c | Curing Time (day) | ($\Delta\rho$/$\rho_o$)$_f$ (%) | $\sigma_f$ (MPa) | $q_2$ | $p_2$ | RMSE (MPa) | $R^2$ |
|---|---|---|---|---|---|---|---|---|
| Cement | 0.38 | 1 | 0.70 | 10.6 | 3.51 | 0.89 | 0.04 | 0.99 |
|  |  | 7 | 0.62 | 15.8 | 0.12 | 0.10 | 0.03 | 0.99 |

TABLE 2-continued

| Material | w/c | Curing Time (day) | ($\Delta\rho$/$\rho_o$)$_f$ (%) | $\sigma_f$ (MPa) | $q_2$ | $p_2$ | RMSE (MPa) | $R^2$ |
|---|---|---|---|---|---|---|---|---|
| only |  | 28 | 0.55 | 17.3 | 0.05 | 0.01 | 0.04 | 0.99 |
|  | 0.44 | 1 | 0.60 | 8.4 | 0.83 | 0.62 | 0.03 | 0.99 |
|  |  | 7 | 0.55 | 13.0 | 1.09 | 0.45 | 0.04 | 0.99 |
|  |  | 28 | 0.41 | 15.1 | 2.35 | 0.00 | 0.04 | 0.99 |
|  | 0.54 | 1 | 0.48 | 4.6 | 0.34 | 0.27 | 0.04 | 0.98 |
|  |  | 7 | 0.41 | 8.9 | 1.14 | 0.00 | 0.02 | 0.99 |
|  |  | 28 | 0.33 | 11.3 | 1.82 | 0.00 | 0.02 | 0.99 |
| Smart cement | 0.38 | 1 | 583 | 10.9 | 0.30 | 0.16 | 0.01 | 0.99 |
|  |  | 7 | 432 | 17.2 | 0.14 | 0.09 | 0.03 | 0.99 |
|  |  | 28 | 401 | 19.4 | 0.05 | 0.03 | 0.03 | 0.99 |
|  | 0.44 | 1 | 531 | 9.8 | 1.59 | 0.85 | 0.02 | 0.99 |
|  |  | 7 | 405 | 13.7 | 0.33 | 0.07 | 0.02 | 0.99 |
|  |  | 28 | 389 | 16.8 | 0.41 | 0.06 | 0.02 | 0.99 |
|  | 0.54 | 1 | 355 | 5.3 | 1.37 | 0.0 | 0.04 | 0.99 |
|  |  | 7 | 325 | 9.2 | 0.41 | 0.0 | 0.03 | 0.99 |
|  |  | 28 | 289 | 12.6 | 0.39 | 0.0 | 0.02 | 0.99 |

The change in electrical resistivity at failure $$\left(\frac{\Delta\rho}{\rho_o}\right)_f$$

for the unmodified oil well cement with different w/c ratios of 0.38, 0.44 and 0.54 were 0.70%, 0.60% and 0.48% respectively as summarized in Table 2. With 0.1% CF addition to the smart cement the electrical resistivity at failure $$\left(\frac{\Delta\rho}{\rho_o}\right)_f$$

for the smart cement with w/c of 0.38, 0.44 and 0.54 were 583%, 531% and 355% respectively. An additional 0.1% CF to the cement substantially enhanced the change in electrical resistivity of oil well cement at failure $$\left(\frac{\Delta\rho}{\rho_o}\right)_f$$

with w/c ratios of 0.38, 0.44 and 0.54 by a factor of 832, 697 and 729 respectively as summarized in Table 2.

Figure 4:
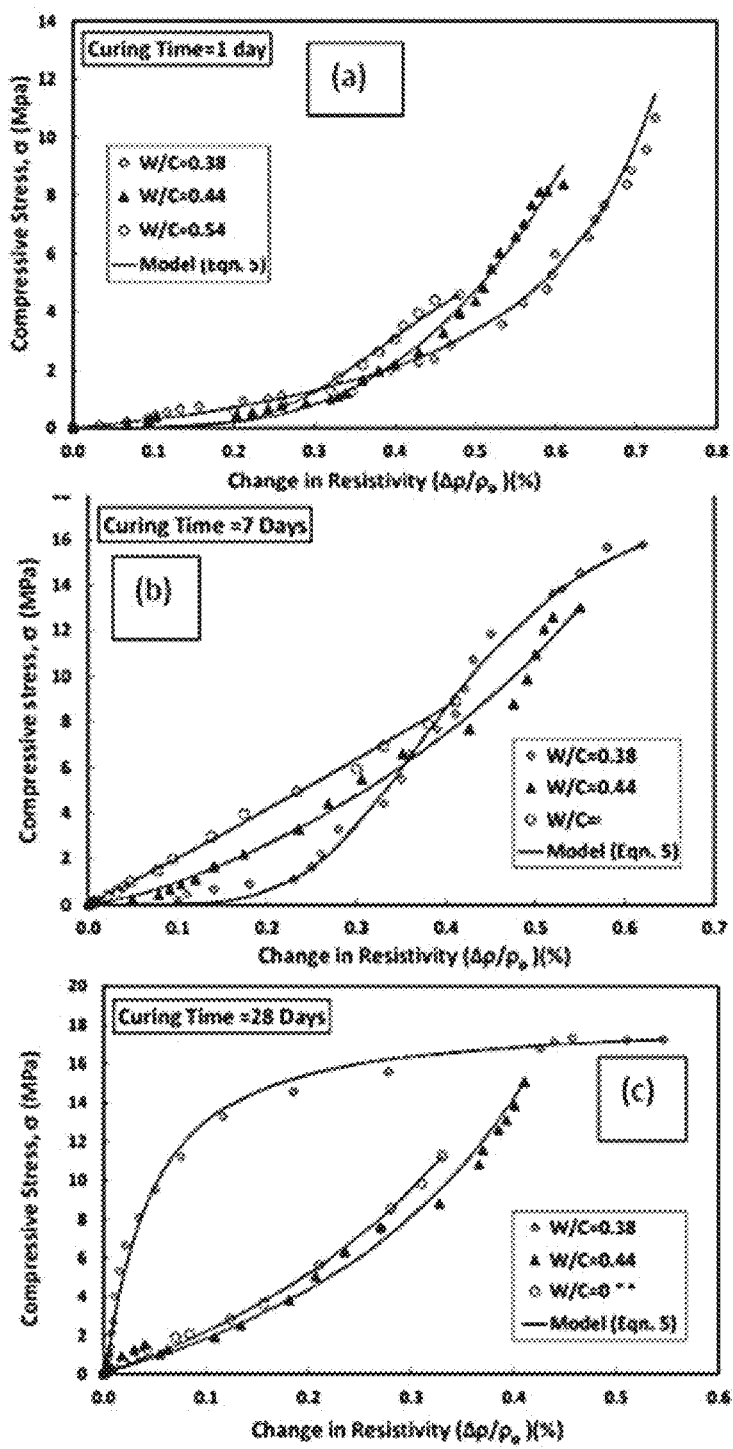
FIG. 4 shows measured and predicted piezoresistive behavior of oil well cement with curing times of (a) 1 day, (b) 7 days, and (c) 28 days.

Using the p-q Piezoresistive constitutive model shown above, the relationships between compressive stress and the change in electrical resistivity $$\left(\frac{\Delta\rho}{\rho_o}\right)$$

of the cement with different w/c ratios of 0.38, 0.44 and 0.54 for one day of curing were modeled. The piezoresistive constitutive model predicted the measured stress-change in resistivity relationship very well (FIGS. 4(*a*) and 5(*a*)). The model parameters $q_2$ and $p_2$ are summarized in Table 2. The coefficients of determination ($R^2$) were 0.98 and 0.99. The root mean square of error (RMSE) varied between 0.02 MPa and 0.04 MPa as summarized in Table 2.

(ii) 7 Days of Curing

The compressive strength ($\sigma_f$) of the cement with w/c ratio of 0.38, 0.44 and 0.54 after 7 days of curing increased by 61%, 56% and 115% respectively compared with the compressive strength ($\sigma_f$) of the cement after one day of curing as summarized in Table 2. Addition of 0.1% CF to the cement (smart cement) with w/c ratio of 0.38, 0.44 and 0.54 increased the compressive strength to 17.2 MPa, 13.7 MPa and 9.2 MPa respectively. Hence the addition of 0.1% CF to the cement increased the compressive strength by 9%, 5% and 4% for cement with w/c ratio of 0.38, 0.44 and 0.54 respectively.

Figure 5:
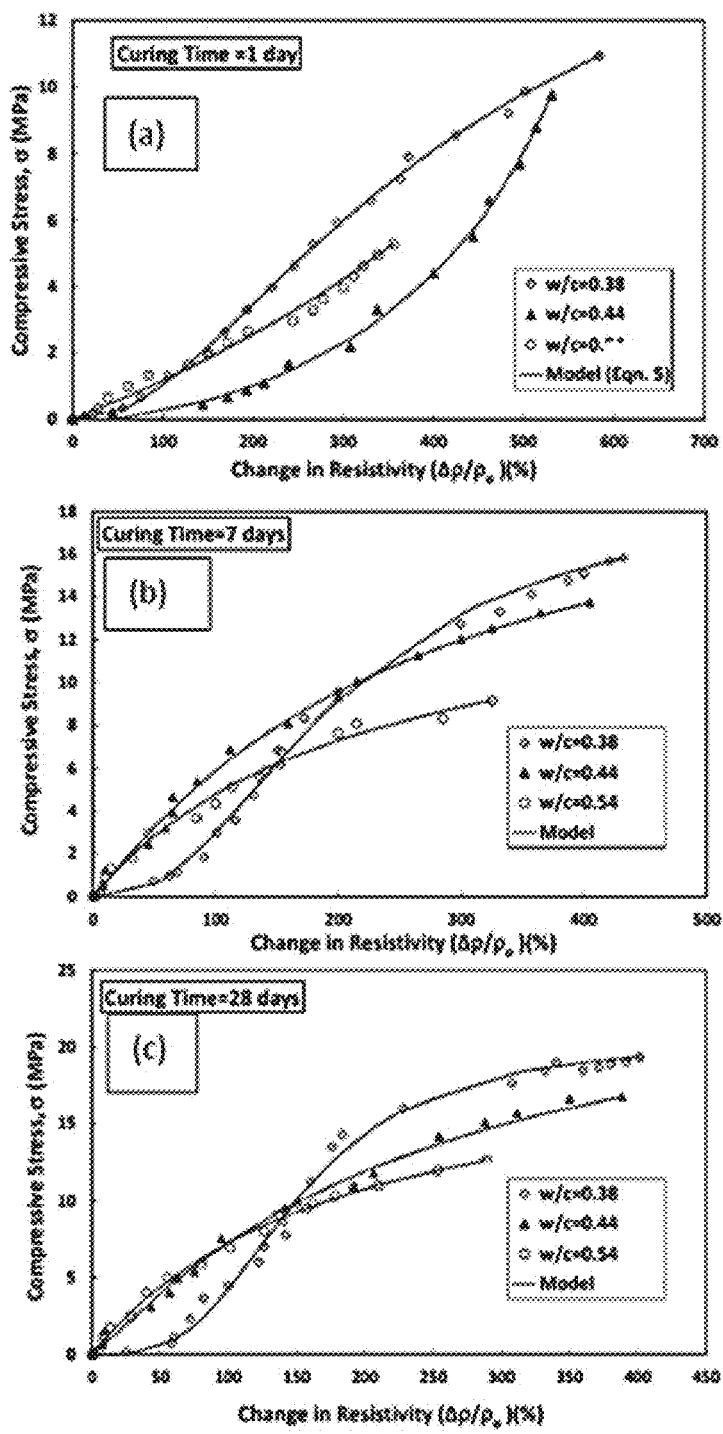
FIG. 5 shows measured and predicted piezoresistive behavior of smart cement with curing times of (a) 1 day, (b) 7 days, and (c) 28 days.

The change in electrical resistivity at failure $$\left(\frac{\Delta\rho}{\rho_o}\right)_f$$

for the unmodified oil well cement with different w/c ratios of 0.38, 0.44 and 0.54 were 0.62%, 0.55% and 0.41% respectively as shown in FIG. 4(b). With 0.1% CF addition to the smart cement the electrical resistivity at failure $$\left(\frac{\Delta\rho}{\rho_o}\right)_f$$

for the smart cement with w/c of 0.38, 0.44 and 0.54 were 432%, 405% and 325% respectively (FIG. 5(b)). An additional 0.1% CF to the cement substantially enhanced the change in electrical resistivity of oil well cement at failure $$\left(\frac{\Delta\rho}{\rho_o}\right)_f$$

with w/c ratios of 0.38, 0.44 and 0.54 by a factor of 697, 736 and 792 respectively as summarized in Table 2.

The relationships between compressive stress and the change in electrical resistivity $$\left(\frac{\Delta\rho}{\rho_o}\right)$$

of the cement with different w/c ratios of 0.38, 0.44 and 0.54 for one day of curing were modeled suing the p-q piezoresistive model. The piezoresistive constitutive model predicted the measured stress-change in resistivity relationship very well (FIGS. 4(b) and 5(b)). The piezoresistive model parameters $q_2$ and $p_2$ are summarized in Table 2. The coefficients of determination ($R^2$) were 0.99. The root mean square of error (RMSE) varied between 0.02 MPa and 0.04 MPa as summarized in Table 2.

(iii) 28 Days of Curing

The compressive strength ($\sigma_f$) of the cement with w/c ratio of 0.38, 0.44 and 0.54 for 28 day of curing increased by 12%, 16% and 14% respectively compared with the 7 day compressive strengths. Addition of 0.1% CF to the cement (smart cement) with w/c ratio of 0.38, 0.44 and 0.54 increased the compressive strength to 19.4 MPa, 16.8 MPa and 12.6 MPa respectively. Hence the addition of 0.1% CF to the cement increased the compressive strength by 12%, 11% and 12% for cement with w/c ratio of 0.38, 0.44 and 0.54 respectively.

The change in electrical resistivity of oil well cement at failure $$\left(\frac{\Delta\rho}{\rho_o}\right)_f$$

with different w/c ratios of 0.38, 0.44 and 0.54 were 0.55%, 0.41% and 0.33% respectively as shown in FIG. 4(c) and summarized in Table 2. With 0.1% CF addition to the cement (smart cement) the electrical resistivity at failure $$\left(\frac{\Delta\rho}{\rho_o}\right)_f$$

for the smart cement with w/c of 0.38, 0.44 and 0.54 were 401%, 389% and 289% respectively (FIG. 5(c)). An additional 0.1% CF to the cement increased the change in electrical resistivity of oil well cement at failure $$\left(\frac{\Delta\rho}{\rho_o}\right)_f$$

with w/c ratios of 0.38, 0.44 and 0.54 by a factor of 729, 948 and 875 respectively as summarized in Table 2.

The relationships between compressive stress and the change in electrical resistivity $$\left(\frac{\Delta\rho}{\rho_o}\right)$$

of the cement with different w/c ratios of 0.38, 0.44 and 0.54 for one day of curing were modeled suing the p-q piezoresistive model. The piezoresistive constitutive model predicted the measured stress-change in resistivity relationship very well (FIGS. 4(c) and 5(c)). The piezoresistive model parameters $q_2$ and $p_2$ are summarized in Table 2. The coefficients of determination ($R^2$) were 0.99. The root mean square of error (RMSE) varied between 0.02 MPa and 0.04 MPa as summarized in Table 2.

In summary, the addition of 0.1% CF to the oil well cement substantially enhanced the piezoresistivity behavior of the cement (over 700 times) to make it very sensing and smart. The model parameters $q_2$ for oil well cement without CF varied between 0.05 and 3.51 based on the w/c ratio and curing time as summarized in Table 2. The model parameters $q_2$ for oil well cement with 0.1% CF varied between 0.05 and 1.59 based on the w/c ratio and curing time as summarized in Table 2. The model parameters $p_2$ for oil well cement without CF varied between 0 and 0.89 based on the w/c ratio and curing time. For the smart cement the parameter $p_2$ varied from 0 to 0.16 (Table 2). Addition of 0.1% CF also improved the compressive strength of the oil well cement.

During the entire cement hydration process both the electrical resistivity and compressive strength of the cement increased gradually with the curing time. For cement pastes with various w/c ratios, the change in resistivity was varied during the hardening. The cement paste with a lower w/c ratio had a lowest electrical resistivity change ($RI_{24\,hr}$) than cement with higher w/c ratio as shown in Table 1.

Figure 6:
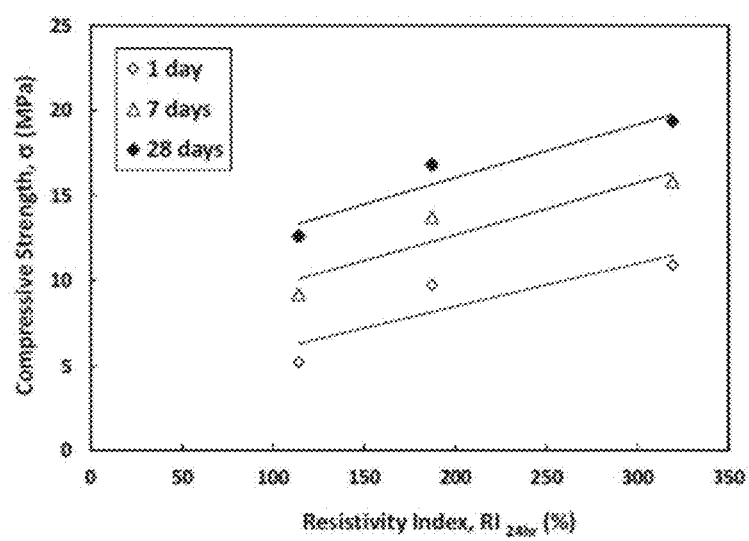
FIG. 6 shows the relationship between resistivity index ($RI_{24\ hr}$) and compressive strength of smart cement for a water-to-cement ratio of 0.38 to 0.54.

The relationship between ($RI_{24\ hr}$) and the one day, 7 days and 28 days compressive strength (MPa) (FIG. 6) were:

$$\sigma_{1\ day}=0.03\times RI_{24\ hr}+3.3\ R^2=0.81$$

$$\sigma_{7\ days}=0.031\times RI_{24\ hr}+6.5\ R^2=0.89$$

$$\sigma_{28\ days}=0.03\times RI_{24\ hr}+9.7\ R^2=0.94$$

Hence the compressive strength of the smart cement after various curing times was linearly related to the electrical resistivity index, $RI_{24\ hr}$. Since $RI_{24\ hr}$ can be determined in one day, it can be used to predict the compressive strength of smart cement up to 28 days.

Based on the experimental study and analytical modeling of the curing and piezoresistivity behavior of smart cement with w/c ratio of 0.38, 0.44 and 0.54, the following conclusions were reached:

(1) The initial resistivity ($\rho_o$) of the smart cement decreased from 1.03 Ω-m to 1 Ω-m and 0.9 Ω-m, a 3% and 12% reduce with increasing the water-to-cement ratio from 0.38 to 0.44 and 0.54 respectively. The changes in the electrical resistivity were higher than the changes in the unit weight of the cement. Hence the electrical resistivity can also be used for quality control.

(2) The smart cement showed enhanced piezoresistive behavior compared to unmodified cement. With 0.1% conductive filler (CF) modification the piezoresistivity at peak stress was enhanced by over 700 times the unmodified cement. The piezoresistivity enhancement was depended on the water-to-cement ratio and curing time. The new piezoresistive constitutive model predicted the compressive stress-changes in resistivity relationship very well. An additional 0.1% CF also increased the 28 day compressive strength by over 10%.

(3) Linear relationship was observed between resistivity index ($RI_{24\ hr}$) and compressive strength of smart cement for different curing times. Since $RI_{24\ hr}$ can be determined in one day, it can be used to predict the compressive strength of smart cement up to 28 days.

(4) The resistivity parameters, minimum resistivity and the time to reach minimum resistivity were linearly related to the water-to cement ratio. Hence these resistivity parameters can also be used for quality control of the smart cement mixtures.

To summarize, the effect of water-to-cement ratio (w/c) on the piezoresistive behavior of smart oil well cement was investigated. The sensing property of the smart cement was modified with 0.1% conductive filler (CF) and the behavior was investigated up to 28 days of curing. Electrical resistivity was identified as the sensing and monitoring property for the smart cement. The initial resistivity ($\rho_o$) of the smart cement decreased from 1.03 Ω-m to 1 Ω-m and 0.9 Ω-m, a 3% and 12% reduction when the w/c ratio was increased from 0.38 to 0.44 and 0.54 respectively, higher than the changes in the initial unit weights of the cement grouts. The minimum resistivity ($\rho_{min}$) of the smart cement also decreased from 0.99 Ω-m to 0.89 Ω-m and 0.78 Ω-m, a 10% and 21% reduction when the w/c ratio was increased from 0.38 to 0.44 and 0.54 respectively. The electrical resistivity of the smart cement after 24 hours of curing ($\rho_{24\ hr}$) decreased by 39% and 60% when the w/c ratio was increased from 0.38 to 0.44 and 0.54 respectively. The electrical resistivity of the smart cement after 7 days of curing ($\rho_{7\ days}$) was higher than the electrical resistivity after one day by 87%, 96% and 175% for the w/c ratio of 0.38, 0.44 and 0.54 respectively. A nonlinear curing model was used to predict the changes in electrical resistivity with curing time and it predicted all the measured trends very well. Also the curing electrical parameters were linearly related to the water-to-cement (w/c) ratio. The piezoresistivity of the smart cement at failure was over 700 times higher than the unmodified cement (less than 0.7%) and was depended on the w/c ratio and curing time and making the cement very sensing. The nonlinear piezoresistive constitutive model predicated the compressive stress-change in resistivity relationship of the smart cement very well. The compressive strength of the smart cement with 0.1% CF and w/c ratio of 0.38, 0.44 and 0.54 were increased by over 10% after 28 days of curing compared to the unmodified cement. Linear correlations were observed between resistivity index ($RI_{24hr}$) and compressive strength of smart cement for different curing times.

EXAMPLE 4

Contaminated Smart Cement

Figure 7:
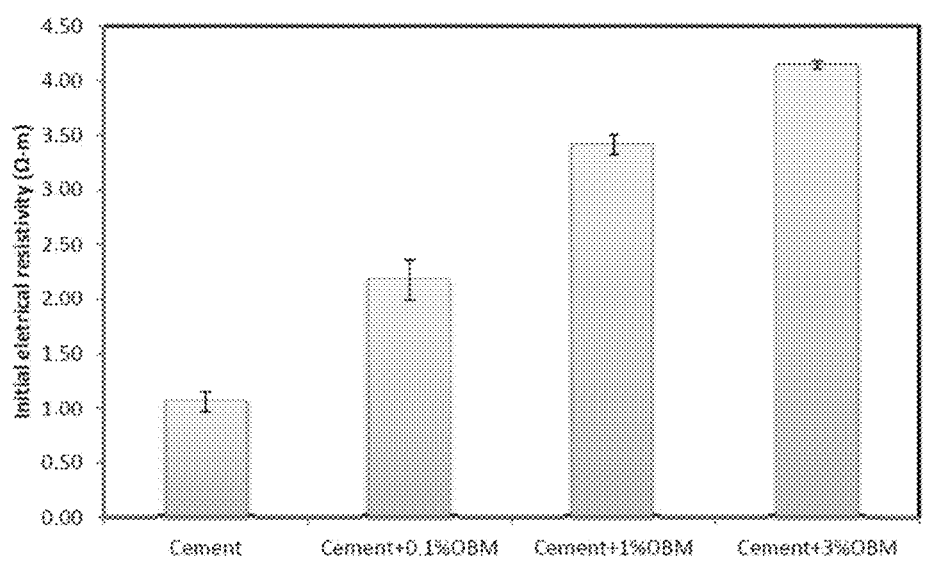
FIG. 7 shows the initial resistivity of cement samples having varying amounts of oil-based mud (OBM) contamination.

The electrical resistivity of uncontaminated and contaminated chemo-thermo-piezoresistive smart cement immediately after preparing the sample is shown in FIG. 7. As shown in FIG. 7, the initial electrical resistivity of the smart cement increased with an increase in the mud contamination. The average initial electrical resistivity of modified uncontaminated cement was 1.06 Ω·m. Contaminating the smart cement with only 0.1 percent of oil-based mud (OBM) increased its initial electrical resistivity to 1.95 Ω·m which was 84 percent higher than the uncontaminated cement. When the smart cement was contaminated with 1 percent and 3 percent OBM, the increment in initial electrical resistivity was more than 216 percent and 304 percent respectively. Hence, electrical resistivity was highly sensitive to OBM contamination, and initial electrical resistivity of cement was a good indicator of OBM contamination.

Figure 8:
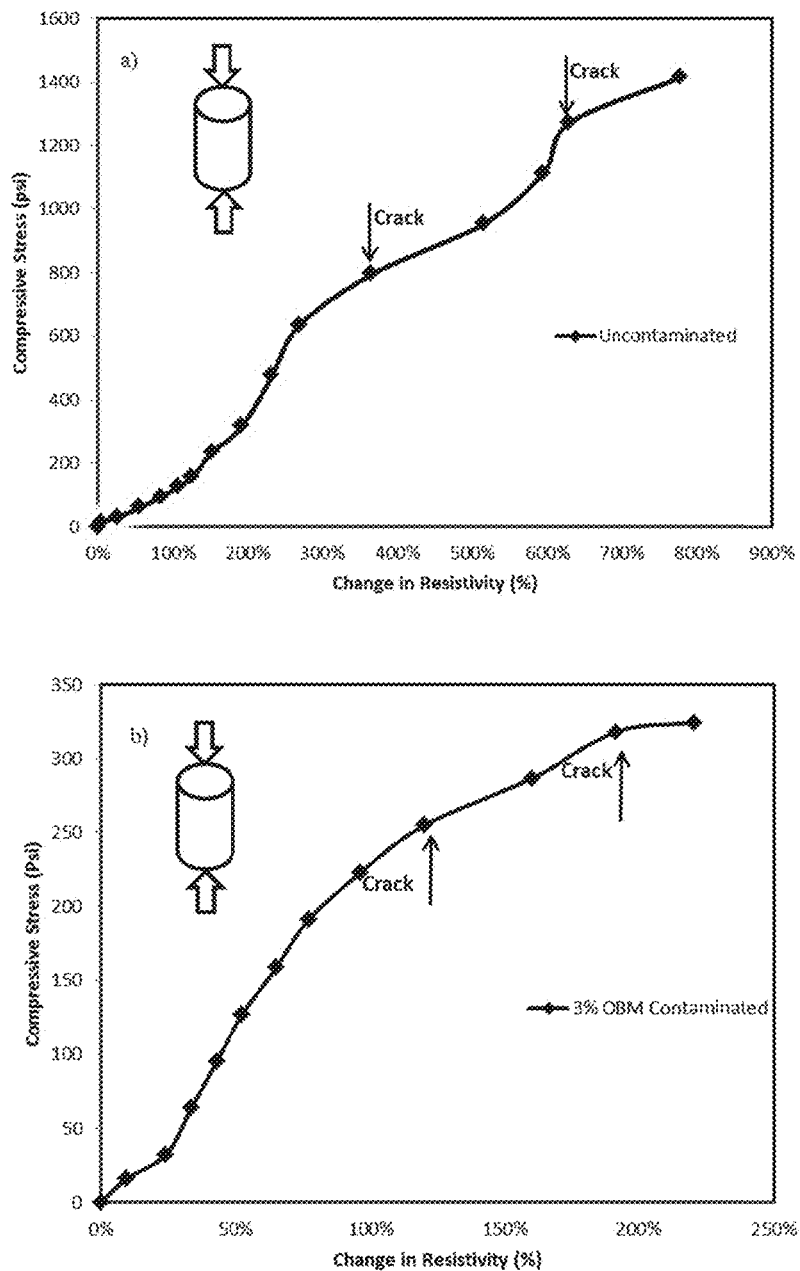
FIG. 8 shows the piezoresistive behavior (compressive stress versus change in resistivity) for (a) uncontaminated and (b) contaminated cement after 1 day of curing.
Figure 9:
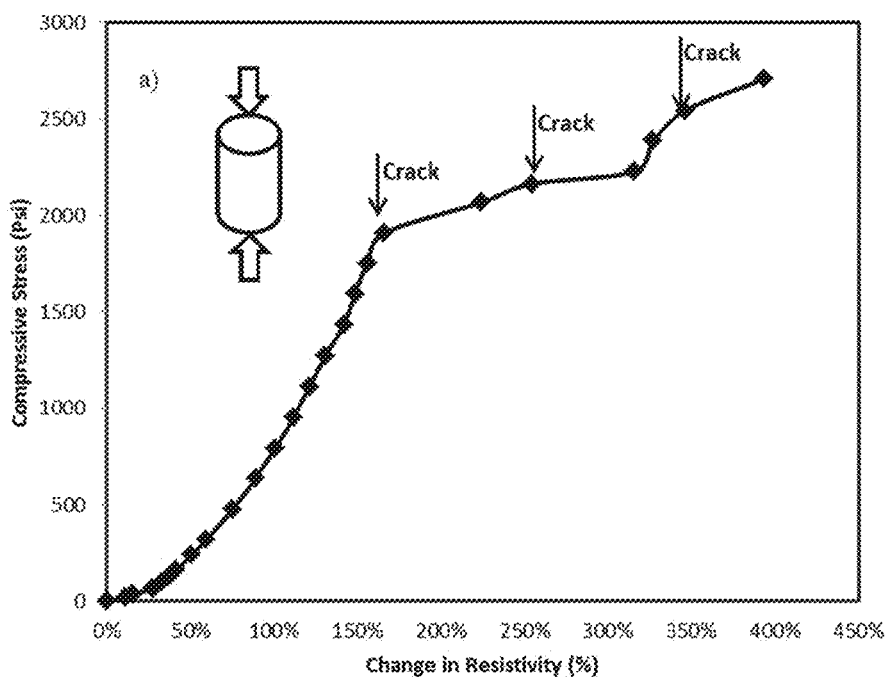
FIG. 9 shows the piezoresistive behavior (compressive stress versus change in resistivity) for (a) uncontaminated and (b) contaminated cement after 28 days of curing.
Figure 9:
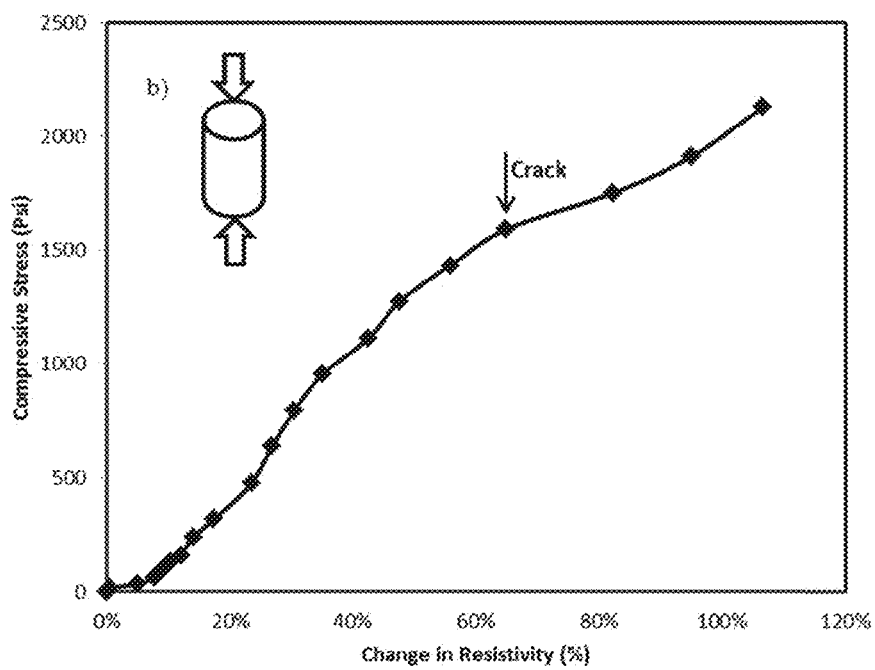

The chemo-thermo-piezoresistive behavior (compressive stress and/or contamination versus change in resistivity) of uncontaminated and contaminated cement is shown in FIGS. 8 and 9, after 1 day and 28 days curing, respectively. Electrical resistivity was sensitive to the compressive stress. FIGS. 8 and 9 show that electrical resistivity increased during compressive loading, and there was a sharp increase with formation of cracks within the specimen. OBM contamination affected the piezoresistive response of smart cement. After one day of curing the uncontaminated smart cement failed at a resistivity change of 780 percent, while the 3% OBM contaminated cement failed at a resistivity change of 220 percent. For the 3% OBM contaminated specimen after 28 days of curing, the change in electrical resistivity at failure was 3 times lower than that of the uncontaminated cement. The smart cement showed chemo-thermo-piezoresistive behavior with and without OBM contamination.

REFERENCES CITED

The following references, to the extent that they provide exemplary procedural or other details supplementary to those set forth herein, are specifically incorporated herein by reference.

NON-PATENT LITERATURE

API Recommended Practice 10B (1997). "Recommended practice for testing well cements" Exploration and Production Department, $22^{nd}$ Edition.

API recommended Practice 65 (2002). "Cementing shallow water flow zones in deepwater wells."

Azhari, F. and Banthia, N. (2012). "Cement-based sensors with carbon fibers and carbon nanotubes for piezoresistive sensing, cement and concrete composites." 34, 866-873.

Chung, D. D. L. (2001). "Functional properties of cement-matrix composites." Material Science, 36, 1315-1324.

Han, B., Zhang, K., Yu, X., Kwon, E. and J. Ou, (2012). "Composites electrical characteristics and pressure-sensitive response measurements of Carboxyl MWNT/cement composites." Cement and Concrete Composites, 34, 794-800.

Izon, D., Mayes, M. (2007). "Absence of fatalities in blowouts encouraging in MMS study of OCS incidents 1992-2006." Well Control, 86-90.

Kyle, M. and Eric, O. (2014). "Improved regulatory oversight using real-time data monitoring technologies in the Wake of Mocondo." SPE 170323, 1-51.

Liao, Y. and Wei, X. (2014). "Relationship between chemical shrinkage and electrical resistivity for cement pastes at early age." Journal of Materials in Civil Engineering, 26, 384-387.

McCarter, W. J. (1996). "Monitoring the influence of water and ionic ingress on cover-zone concrete subjected to repeated absorption, Cement Concrete and Aggregates." 18, 55-63.

McCarter, W. J., Starrs, G., and Chrisp, T. M. (2000). "Electrical conductivity, diffusion, and permeability of Portland cement-based mortars." Cement and Concrete Research, 30, 1395-1400.

Mohammed, A. and Vipulanandan, C. (2014). "Compressive and tensile behaviour of polymer treated sulfate contaminated CL soil, Geotechnical and Geological Engineering, 32, 71-83.

Usluogullari, O. and Vipulanandan, C. (2011). "Stress-strain behavior and California bearing ratio of artificially cemented sand" Journal of Testing and Evaluation, 39, 1-9.

Vipulanandan, C. and Paul, E., 1990. "Performance of Epoxy and Polyester Polymer Concrete". ACI Materials Journal, Vol. 87, No. 3, May-June, 1990, p. 241-251.

Vipulanandan, C. and Liu, J. (2002). "Film Model for Coated Cement Concrete." Cement and Concrete Research, Vol. 32(4), 1931-1936.

Vipulanandan, C., Ahossin, Y. J. and Bilgin, O. (2007). "Geotechnical properties of marine and deltaic soft clays." GSP 173 Advances in Measurement and Modelling of Soil Behaviour, 1-13.

Vipulanandan, C. and Garas, V. (2008). "Electrical resistivity, pulse velocity and compressive properties of carbon fiber reinforced cement mortar." Journal of Materials in Civil Engineering, 20, 93-101.

Vipulanandan, C. and Prashanth, P. (2013). "Impedance spectroscopy characterization of a piezoresistive structural polymer composite bulk sensor." Journal of Testing and Evaluation, 41, 898-904.

Vipulanandan, C, Krishnamoorti, R. Saravanan, R. Qi, Q. and Pappas, J. (2014a) "Development of Smart Cement for Oil well Applications", Offshore Technology Conference (OTC) 2014, OTC-25099-MS, CD Proceeding, 1-18.

Vipulanandan, C., Heidari, M., Qu, Q., Farzam, H. and Pappas, J. M. (2014b). "Behavior of piezoresistive smart cement contaminated with oil based drilling mud." Offshore Technology Conference, OTC 25200-MS, 1-14.

Vipulanandan, C, Ali, K. and Pappas, J. (2014c) "Smart Cement Modified with Meta Silicate For Oil Well Cementing," American Association of Drilling Engineers (AADE), 2014, AADE-14-NTCE-03, CD Proceeding, Houston, Tex., April 2014.

Vipulanandan, C. and Mohammed, A. (2014d). "Hyperbolic rheological model with shear stress limit for acrylamide polymer modified bentonite drilling muds." Petroleum Science and Engineering, 122, 38-47.

Wei, X., Lianzhen, X. and Li, Z. (2008). "Electrical measurement to assess hydration process and the porosity formation." Journal of Wuhan University of Technology-Material Science. Ed., 23, 761-766.

Zhang, J., Weissinger, E. A., Peethamparan, S. and Scherer, G. W. (2010). "Early hydration and setting of oil well cement." Cement and Concrete research, 40, 1023-1033.

Zuo, Y., Zi, J. and Wei, X. (2014). "Hydration of cement with retarder characterized via electrical resistivity measurements and computer simulation." Construction and Building Materials, 53, 411-418.

What is claimed is:

1. A system for monitoring performance-related properties of cement, comprising:
a cement structure comprised of chemo-thermo-piezoresistive smart cement, wherein the chemo-thermo-piezoresistive smart cement comprises from about 0.03% to about 0.1% modified conductive or semi-conductive filler by weight of the chemo-thermo-piezoresistive smart cement, and wherein the modified conductive or semi-conductive filler comprises dispersed carbon fibers, dispersed basaltic fibers, or mixtures thereof; and
an integrated real-time monitoring system for monitoring changes in electrical resistivity of the chemo-thermo-piezoresistive smart cement, wherein the changes in the electrical resistivity of the chemo-thermo-piezoresistive smart cement correlate with performance-related properties of the chemo-thermo-piezoresistive smart cement, wherein the integrated real-time monitoring system collects AC resistance measurements at selected frequencies, wherein the integrated real-time monitoring system uses the AC resistance measurements to calculate the changes in the electrical resistivity and changes in electrical impedance of the chemo-thermo-piezoresistive smart cement using an equivalent circuit to represent electrical properties of the chemo-thermo-piezoresistive smart cement, wherein the chemo-thermo-piezoresistive smart cement is represented in the equivalent circuit as a bulk material with contacts as follows:

$$Z_2(\sigma) = R_b(\sigma) + \frac{2R_c(\sigma)}{1+\omega^2 R_c^2 C_c^2} - j\frac{2\omega R_c^2 C_c(\sigma)}{1+\omega^2 R_c^2 C_c^2},$$

wherein $Z_2$ is total electrical impedance for the equivalent circuit, $R_b$ is resistance of the bulk material, $R_c$ is resistance of the contacts, $C_c$ is capacitance of the contacts, and $\omega$ is a selected frequency, and wherein the equivalent circuit assumes a negligible capacitance for the bulk material.

2. The system of claim 1, wherein the performance-related properties of the smart cement comprise curing, compressive strength, induced stresses, water-to-cement ratio, temperature changes, fluid loss, and contamination of the chemo-thermo-piezoresistive smart cement.

3. The system of claim 1, wherein the changes in the electrical resistivity of the chemo-thermo-piezoresistive smart cement correlate with performance-related properties of the cement with and without contamination.

4. The system of claim 1, wherein the cement structure is part of an oil or gas well.

5. The system of claim 1, wherein the cement structure is part of civil infrastructures selected from the group consisting of footings, piles, pipelines, buildings, tunnels, bridges, and highways.

6. The system of claim 1, wherein the chemo-thermo-piezoresistive smart cement is part of grout, concrete, a coating, or a repair material.

7. A method for real-time monitoring of performance-related properties of cement, comprising:
constructing a cement structure, wherein the cement structure comprises chemo-thermo-piezoresistive smart cement and an integrated real-time monitoring system for monitoring changes in electrical resistivity of the chemo-thermo-piezoresistive smart cement, wherein the chemo-thermo-piezoresistive smart cement comprises from about 0.03% to about 0.1% modified conductive or semi-conductive filler by weight of the chemo-thermo-piezoresistive smart cement, and wherein the modified conductive or semi-conductive filler comprises dispersed carbon fibers, dispersed basaltic fibers, or mixtures thereof;
collecting AC resistance measurements of the chemo-thermo-piezoresistive smart cement at selected frequencies using the integrated real-time monitoring system;
using the AC resistance measurements to calculate changes in the electrical resistivity of the chemo-thermo-piezoresistive smart cement and changes in electrical impedance of the chemo-thermo-piezoresistive smart cement using an equivalent circuit to represent electrical properties of the chemo-thermo-piezoresistive smart cement, wherein the chemo-thermo-piezoresistive smart cement is represented in the equivalent circuit as a bulk material with contacts as follows:

$$Z_2(\sigma) = R_b(\sigma) + \frac{2R_c(\sigma)}{1+\omega^2 R_c^2 C_c^2} - j\frac{2\omega R_c^2 C_c(\sigma)}{1+\omega^2 R_c^2 C_c^2},$$

wherein $Z_2$ is total electrical impedance for the equivalent circuit, $R_b$ is resistance of the bulk material, $R_c$ is resistance of the contacts, $C_c$ is capacitance of the contacts, and $\omega$ is a selected frequency, and wherein the equivalent circuit assumes a negligible capacitance for the bulk material; and
monitoring the changes in the electrical resistivity and the electrical impedance of the chemo-thermo-piezoresistive smart cement using the integrated real-time monitoring system, wherein the changes in the electrical resistivity of the chemo-thermo-piezoresistive smart cement correlate with performance-related properties of the chemo-thermo-piezoresistive smart cement.

8. The method of claim 7, wherein the changes in the electrical resistivity of the chemo-thermo-piezoresistive smart cement correlate with performance-related properties of the cement with and without contamination.

9. The method of claim 7, wherein the performance-related properties of the cement comprise curing, compressive strength, induced stresses, water-to-cement ratio, temperature changes, fluid loss, and contamination of the chemo-thermo-piezoresistive smart cement.

10. The method of claim 7, wherein the cement structure is part of an oil or gas well.

11. The method of claim 7, wherein the cement structure is part of civil infrastructures selected from the group consisting of footings, piles, pipelines, buildings, tunnels, bridges, and highways.

12. The method of claim 7, wherein the chemo-thermo-piezoresistive smart cement is part of grout, concrete, a coating, or a repair material.

* * * * *